United States Patent [19]

Ibsen et al.

[11] 4,297,266

[45] Oct. 27, 1981

[54] MICROFILLED DENTAL COMPOSITE AND METHOD USING THE SAME

[75] Inventors: Robert L. Ibsen; William R. Glace, both of Santa Maria, Calif.

[73] Assignee: Den-Mat, Inc., Santa Maria, Calif.

[21] Appl. No.: 120,119

[22] Filed: Feb. 8, 1980

[51] Int. Cl.³ .................. A61K 6/08; C08K 3/26; C08K 3/40; C08K 9/06

[52] U.S. Cl. .................. 260/42.14; 106/35; 260/42.15; 260/42.52; 260/42.53; 260/998.11

[58] Field of Search ............. 260/42.52, 42.15, 42.53, 260/998.11, 42.14; 106/35

[56] References Cited

U.S. PATENT DOCUMENTS

| | | | |
|---|---|---|---|
| 3,770,811 | 11/1973 | Lee, Jr. et al. | 260/998.11 |
| 3,926,906 | 12/1975 | Lee, II et al. | 106/35 |
| 4,032,504 | 6/1977 | Lee, Jr. et al. | 106/35 |
| 4,150,012 | 4/1979 | Joos | 260/42.15 |

OTHER PUBLICATIONS

McLean, *Journal of Prosthetic Dentistry*, vol. 42, No. 2, Aug. 1979, pp. 154–156.

Raptis et al., Jada, vol. 99, Oct. 1979, pp. 631–633.

*Primary Examiner*—Allan Lieberman
*Attorney, Agent, or Firm*—Owen, Wickersham & Erickson

[57] ABSTRACT

A filled-resin dental composite. The filler is a mixture of hydrophobic silica particles about 0.01 to 0.04 micron in diameter and glass particles about 2 to 30 microns in diameter. Preferably, the glass is x-ray opaque. An improved method for restoring carious lesions in a living tooth is presented, using the composite.

11 Claims, No Drawings

MICROFILLED DENTAL COMPOSITE AND METHOD USING THE SAME

This invention relates to a microfilled dental composite and to a method employing it.

Heretofore the fillers in dental composites have been composed of particles from about 0.5 micron to about 150 microns in diameter. These relatively large particles have resulted in a rougher type of finish than many practitioners desire. Yet, although some manufacturers used a small amount of submicron filler particles, which are typically 0.02 to 0.04 micron in diameter (to eliminate settling, for example), they have used them only up to about 5% by weight of the composite, and most of the particles remained relatively large.

Recently, various manufacturers have placed on the market "microfilled" composites in which all of the filler was in the 0.02 to 0.04 micron range, and a smoother finish was thereby obtained. However, when using these small-particle fillers, only about 25% to 50% of the composite could be filler. This fact led to the disadvantage that the overall composite exhibited a much greater cure shrinkage than previous composites using large-particle fillers, so that the composite tended to pull away from the teeth as it cured. Such composites have also had a higher coefficient of thermal expansion and higher water sorption than those of the regular composites containing larger sized particles.

SUMMARY OF THE INVENTION

The present invention provides a microfilled dental composite containing from about 30% to about 83.5% filler, and the filler is a mixture of (1) sub-micron hydrophobic silica particles about 0.01–0.04 micron in diameter and (2) glass particles in the range of 2 to 30 microns. Weightwise the glass is present in amounts equal to or in excess of the sub-micron filler; however, due to the density differences, most of the filler, in terms of volume, is sub-micron hydrophobic silica. Preferably, the glass should contain barium or strontium, to render it x-ray opaque.

An important result obtained by this new composite is that it gives a much smoother finish than do regular composites. Although this finish may not be quite as smooth as can be obtained by the best of the microfilled composites when examined with a scanning electron microscope, the smoothness is quite adequate clinically, and the composition is better overall, for, in contrast to the microfilled products, the chemical and mechanical properties of this new dental composite are not significantly degraded in relation to the conventional composites.

Moreover, there is another advantage, in that the new material is opaque to x-rays, and the regular microfilled compositions are not.

EXAMPLES OF PREFERRED EMBODIMENTS

The system is preferably prepared and stored as a two-paste system with all compositions being present in the two pastes in identical proportions, except that in one of the pastes there is a curing agent or catalyst (e.g., benzoyl peroxide) and in the other paste there is an accelerator, such as 2-hydroxyethyl-p-toluidine. Just before use, the two halves are mixed together and immediately start curing, so that they are emplaced at once.

EXAMPLE 1

A formulation system embodying this invention comprises the following illustrative ranges:

| Component | Parts by Weight |
| --- | --- |
| Ethoxylated bisphenol A dimethacrylate | 53.00–17.5 |
| Triethylene glycol dimethacrylate | 4.00–13.5 |
| Ultra-violet light absorbent (e.g. 2-hydroxy-4-methoxy benzophenone) | 0.4–1.4 |
| Anti-oxidant (e.g. butyl hydroxy toluene) | 0.15–0.5 |
| Curing agent (e.g. benzoyl peroxide) | 0.25–1.00 |
| Cure accelerator (e.g. 2-hydroxyethyl-p-toluidine) | 0.25–1.00 |
| Sub-micron hydrophobic silica particles | 10.00–30.00 |
| Glass particles | 20.00–67.00 |

The sub-micron hydrophobic silica may be Degussa's Aerosil, R 972, which has a particle range of 0.01 to 0.04 microns, with an average particle size of approximately 0.02 micron ($20 \times 10^{-7}$ cm). The basis for the manufacture of hydrophobic silica is a very pure form of silicon dioxide aerosol obtained by flame hydrolysis. Its particles vary in diameter between 10 and 40 m$\mu$. On each 100 sq. meters of surface area, it has about 0.5 millimol silanol groups; hence it is hydrophilic. On its surface there is a one silanol group per 28–33 $A^2$ ($\equiv$Si—OH). Hence, with 200 square meters per gram specific surface area, there are about $6.2 \times 10^{20}$ silanol groups per gram, i.e., one millimol. This gives a figure of about 2000 silanol groups per particle.

In a continuous process, some 75% of these silanol groups can be chemically reacted with dimethyl dichlorosilane, the resultant product having about 0.7 millimol of chemically combined methyl groups per 100 square meters of surface area. The silica when thus reacted becomes hydrophobic and behaves differently in organic liquids from the hydrophilic material. For this purpose, freshly obtained hydrophilic silica is separated from the bulk of the hydrochloric acid formed in the flame hydrolysis. Then, this silica, dimethyl dichlorosilane, and steam are pneumatically fed in parallel flow into a fluidized bed reactor heated to about 400° C. by means of an inert gas such as nitrogen. Besides the chemical reaction of the chlorosilane with the silanol groups of the surface, the desorption of the hydrochloric acid resulting from the reaction takes place in the reactor in a continuous stream, so that there is an analytically assessable chlorine content of below 0.03%. The main quantity of hydrochloric acid is removed from the freshly manufactured $SiO_2$ and the material does not yet contain any absorbed water. Moreover, siloxane bridges still exist on the surface of the particles, these having formed at the high temperatures used in the process. These bridges break up in the presence of water vapor and chlorosilane in the reaction zone, whereupon the reaction can take place in the nascent state of the silanol group formation.

Analytical data and moisture absorption data of hydrophobic silica are given in Tables 1 and 2 respectively.

TABLE 1

| Analytical data on hydrophobic AEROSIL R 972: | |
| --- | --- |
| $SiO_2 + (-CH_3)$ | 99.8% |
| surface area (acc. to Brunauer, Emmet & Teller) | $120 \pm 30$ m$^2$/g |

TABLE 1-continued

| Analytical data on hydrophobic AEROSIL R 972: | |
|---|---|
| average particle size | $20 \pm 10^{-7}$ cm |
| carbon | $1.1 \pm 0.2\%$ |
| pH value (4% dispersion methanol/water 1:1) | $3.8 \pm 0.2$ |
| chlorine content | $0.04 \pm 0.01\%$ |
| heavy metals | 0.003% |
| As | 0.0001% |
| $Fe_2O_3$ | 0.003% |
| $Al_2O_3$ | 0.05% |
| $TiO_2$ | 0.03% |
| $Na_2O$ | 0.01% |
| bulk density | about 40-60 g/l |
| compacted volume | about 20 ml/g |

TABLE 2

| Moisture adsorption in mg/100 $m^2$ | | | | |
|---|---|---|---|---|
| Relative air humidity in % | 20 | 40 | 60 | 80 |
| Hydrophilic silica | 1.3 | 4.0 | 10 | 30 |
| Hydrophobic silica | 0.3 | 0.4 | 0.9 | 1.5 |

The glass particles are preferably x-ray opaque and for that reason preferably contain barium or strontium. The ratio of glass particles to silica particles may vary from about 1:2 to 3:1.

A preferred barium-containing glass may be Kimble's Ray-Sorb T-2000, which has a particle range of 2 to 30 microns, as shown in Table 3.

TABLE 3

| Particle Size Distribution of Ray-Sorb T-2000 | |
|---|---|
| Size | Specification |
| 2 microns | 85-100% greater |
| 5 microns | 60-85% greater |
| 10 microns | 35-60% greater |
| 20 microns | 10-25% greater |
| 30 microns | 0-10% greater |
| This material has the following properties: | |
| Refractive Index: | 1.58 |
| Thermal Expansion: | 6.7 ppm/°C. (0-38° C.) |
| Density: | 3.4 g/cc |

Another suitable radiopaque filler is Kimble's Ray-Sorb T-3000, which has the same particle size distribution as that in Table 3 and which has the following somewhat different properties:
Refractive Index: 1.557
Thermal Expansion: $44.4 \times 10^{-7}$ (0°-38° C.)
Density: 3.049 g/cc A third suitable radiopaque filler, Ray Sorb T-4000, also has the same particle size distribution.

A filler which is not radiopaque is structurally as satisfactory, lacking only the disadvantage of not being radiopaque. For example, Kimble's Cer-Vit T-1000 has the same particle size distribution as that of Table 3 and the following properties:
Thermal Expansion: −2.3 ppm/°C. (0°-38° C.)
Refractive Index: 1.54
Density: 2.5 g/cc The 2-hydroxyethyl-p-toluidine (HEPT) is an accelerator. Other accelerators which may be used include N,N-3,5-tetramethylaniline at about half the concentration of HEPT and N,N-dimethyl-p-toluidine at about one quarter to one half of the concentration of HEPT given above.

Benzoyl peroxide is a curing agent. Other organic peroxide curing agents may be used. Ultra-violet curing agents such as benzoin methyl ether may also be used, in which case no ultra-violet absorber is included.

The 2-hydroxy-4-methoxy benzophenone is an ultraviolet-light absorbent and may be UV-5411.

EXAMPLE 2

Some other systems have been tried in which the ethoxylated bisphenol A dimethacrylate is replaced by Bis-GMA. An example of this is as follows:

| | Parts by Weight |
|---|---|
| Bis-GMA | 36. |
| Triethylene glycol dimethacrylate | 24. |
| Sub-micron hydrophobic silica | 20. |
| Barium-containing glass | 20. |

EXAMPLE 3

| | Parts by Weight |
|---|---|
| Bis-GMA | 28.6 |
| Triethylene glycol dimethacrylate | 19.0 |
| Sub-micron hydrophobic silica | 14.3 |
| Barium-containing glass | 38.1 |

Other examples using the resins of Example 1 follow:

EXAMPLE 4

| | |
|---|---|
| Triethylene glycol dimethacrylate | 11.27 |
| Ethoxylated Bisphenol A dimethacrylate | 16.90 |
| Sub-micron hydrophobic silica | 19.72 |
| Barium-containing glass | 52.11 |

EXAMPLE 5

| | |
|---|---|
| Ethoxylated bisphenol A dimethacrylate | 21.31 |
| Triethylene glycol dimethacrylate | 5.33 |
| 2-hydroxy-4-methoxybenzophenone | 0.53 |
| Butyl hydroxy toluene | 0.18 |
| Benzoyl peroxide | 0.40 |
| 2-hydroxyethyl-p-toluidine | 0.40 |
| Sub-micron hydrophobic silica | 20.00 |
| Barium-containing glass | 52.00 |

When used as a two-paste system, each of the two pastes contains half of the amounts shown in each example, except that only one of the two pastes contains the benzoyl peroxide and the other one includes the 2-hydroxyethyl-p-toluidine. The two pastes may be stores and are mixed just prior to application and applied at once; they set to a gel in about one and one-half to two and one-half minutes.

The material of Example 5 has been compared with one excellent non-microfilled dental composite and with four competing microfilled composites. The test results are shown in Table 4:

TABLE 4

| | Time For Gel Set (Seconds) | Compressive Strength (psi) | Cure Shrinkage (%) | Thermal Expansion (ppm/°C.)* | Water Sorption (mg/$cm^2$) | Color Stability | X-Ray Opacity |
|---|---|---|---|---|---|---|---|
| An excellent | | | | | | | |

TABLE 4-continued

| | Time For Gel Set (Seconds) | Compressive Strength (psi) | Cure Shrinkage (%) | Thermal Expansion (ppm/°C.)* | Water Sorption (mg/cm$^2$) | Color Stability | X-Ray Opacity |
|---|---|---|---|---|---|---|---|
| Non-microfilled dental composite | 120/150 | 36000 | 0.92 | 22 | 0.45 | Exc. | Yes |
| The dental composite of this invention | 120/150 | 36000 | 0.71 | 29 | 0.45 | Exc. | Yes |
| 1st competing microfilled composite | 120/143 | ** | 1.29 | 55 | 1.33 | Poor | No |
| 2nd Competing microfilled composite | 113/175 | 27000 | 1.16 | 76 | 2.10 | Med | No |
| 3rd Competing microfilled composite | 113/175 | 27000 | 1.16 | 76 | 2.10 | Med | No |
| 4th competing microfilled composite | 102/134 | 33000 | 0.84 | 46 | 1.22 | Med | No |

*Over range of 5°–55° C.
**Material very soft, changes cross-section prior to rupture - unable to measure.

As these tests show, the compressive strength of the dental composite of this invention is substantially greater than that of the four competing microfilled composites and equal to that of an excellent non-microfilled composite. The cure shrinkage is lower than that of any of the microfilled composites—much less than three of them—and is less than that of the non-microfilled composite tested. Thermal expansion is not much greater than that of the tested non-microfilled composite and much less than that of any of the microfilled composite. Water sorption is equal to that of the non-microfilled composite and very much less than that of the competing microfilled composites. Furthermore, color stability is excellent, and the composite is opaque to x-rays.

An advantage of this invention is that the consistency of the highly filled material, when the total filler content is about 30% to 83.5% of the total composite, is such that the dentist can use an amalgam carrier for putting it into the cavity. This is much more convenient than the instruments customarily used to place composite restoratives.

Water sorption with the system is below 0.5 mg/cm$^2$, even with only 30% filler. It remains low throughout the filler range at every concentration tested up to 72% total filler with 2.6:1 barium glass:submicron silica.

The compressive strength measured 36,000 p.s.i. at 56% total filler and 2:1 barium glass:aerosil. It remained at 36,000 at 72% total filler and 2.6:1 barium glass:submicron silica.

All samples tested gave less than 0.8% shrinkage. A test with 72% total filler at 2.6:1 barium glass:aerosil gave 0.71% shrinkage.

With 56% filler at 2:1 barium glass:submicron silica, the thermal expansion is 28.85 ppm/°C. With 72% filler at 2.6:1 barium glass:submicron silica, the thermal expansion is 29 ppm/°C.

The radiopaquing effect of the barium glass becomes useful at about 20% barium glass, regardless of total filler concentration.

In use, the dentist prepares by either (1) drilling the cavity and placing retention in the dentin, or (2) by isolating the tooth (i.e., by a rubber dam with a hole for that tooth) and then polishing with pumice to remove plaque and debris, following by washing and drying, and then etching for one or two minutes, typically with 30% to 50% phosphoric acid solution.

In either event, the cavity is then cleaned, as by washing, and is then dried with air, preferably using a drying agent to assist and speed up the drying. Then a bonding agent is applied to the surface of the cavity; this may be a suitable bonding resin of known type. The excess resin is then blown out.

The microfilled dental composite of this invention is then applied, freshly mixed. The cavity is somewhat overfilled, i.e. the composite is applied in excess, using a matrix or other aid where needed to achieve accurate molding. It is then allowed to harden. When it is hardened, the composite is then finished as by diamond, etc., grinding off the excess.

This material may also be utilized as a veneering paste in the laboratory. For example, a cast gold crown was prepared to accept a plastic veneer, utilizing procedures well known to dental laboratory technicians. A veneer was fashioned, utilizing a material like that in Example 5, except that it contained only the peroxide half of the peroxide-amine curing system. The resultant preparation was heat-cured in a dental flask at 100 p.s.i. pressure and at 115° C. for one half hour. The resultant veneer was very hard, smooth, impervious to fluids, and lifelike in appearance. It is possible to prepare special tinted versions of this paste in order to duplicate incisal or dentinal shadings as is commonly done by the dental technician with those materials now used for this purpose.

What is claimed is:

1. A filled-resin dental composite consisting essentially of

| Component | Parts by Weight |
|---|---|
| Ethoxylated bisphenol A dimethacrylate | 53–17.5 |
| Triethylene glycol dimethacrylate | 4–13.5 |
| Cure accelerator | 0.25–1.0 |
| Antioxidant | 0.15–0.5 |
| Curing agent | 0.25–1.0 |
| Ultra violet light absorbent | 0.4–1.4 |
| Sub-micron hydrophobic silica particles | 10–30 |
| Glass particles | 20–67, | the silica particles ranging from about 0.1 micron to 0.04 micron in diameter and the glass particles ranging from about two to about thirty microns in diameter.

2. The dental composite of claim 1 wherein the glass is x-ray opaque.

3. A veneering dental paste for heat curing consisting essentially of

| Component | Parts by weight |
|---|---|
| Ethoxylated bisphenol A dimethacrylate | 53–17.5 |
| Triethylene glycol dimethacrylate | 4–13.5 |
| Antioxidant | 0.15–0.5 |

| Component | Parts by weight |
| --- | --- |
| Benzoyl peroxide | 0.25-1.00 |
| Ultra-violet light absorbent | 0.25-1.00 |
| Sub-micron hydrophobic silica particles | 10-30 |
| Glass particles | 20-67, | the silica particles ranging from about 0.01 micron to 0.04 micron in diameter and the glass particles ranging from about two to about thirty microns in diameter.

4. The dental paste of claim 3 wherein the glass is x-ray opaque.

5. A filled-resin composite consisting essentially of

| Component | Parts by Weight |
| --- | --- |
| Ethoxylated bisphenol A dimethacrylate | 53-17.5 |
| Triethylene glycol dimethacrylate | 4-13.5 |
| 2-hydroxy-4-methoxy benzophenone | 0.4-1.5 |
| Butyl hydroxy toluene | 0.15-0.5 |
| Benzoyl peroxide | 0.25-1.0 |
| 2-hydroxyethyl-p-toluidine | 0.25-1.0 |
| Sub-micron hydrophobic silica particles | 10-30 |
| Barium-containing glass particles | 20-67, | the particles size of the silica being in the range of about 0.01-0.04 micron and the particle size of the glass in the range of about two to thirty microns, averaging about seven microns.

6. A microfilled dental composite consisting essentially of

| Ingredient | Approximate Parts by Weight |
| --- | --- |
| Ethoxylated bisphenol A dimethacrylate | 21 |
| Triethylene glycol dimethacrylate | 5 |
| 2-hydroxy-4-methoxybenzophenone | 0.5 |
| Butyl hydroxy toluene | 0.2 |
| Benzoyl peroxide | 0.4 |
| 2-hydroxyethyl-p-toluidine | 0.4 |
| sub-micron hydrophobic silica particles | 20 |
| Glass particles | 52, | the particle sizes of the fillers being approximately:
silica 0.01-0.04 micron
glass 2-30 microns.

7. The dental composite of claim 6 wherein the glass contains a barium compound in an amount to render it x-ray opaque.

8. A microfilled dental composite consisting essentially of

| Ingredient | Approximate Parts by Weight |
| --- | --- |
| Triethylene glycol dimethacrylate | 11 |
| Ethoxylated bisphenol A dimethacrylate | 16.9 |
| Sub-micron-hydrophobic silica particles | 19.7 |
| Glass particles | 52.1, | silica 0.01-0.04 micron
glass 2-30 microns.

9. The dental composite of claim 8 wherein the glass is x-ray opaque.

10. A microfilled dental composite consisting essentially of

| Component | Approximate Parts by Weight |
| --- | --- |
| Bis-GMA | 36 |
| Triethylene glycol dimethacrylate | 24 |
| Sub-micron hydrophobic silica particles | 20 |
| Glass particles | 20, | the particle sizes being approximately:
silica 0.01-0.04 micron
glass 2-30 microns.

11. The dental composite of claim 10 wherein the glass is x-ray opaque.

* * * * *

UNITED STATES PATENT AND TRADEMARK OFFICE
CERTIFICATE OF CORRECTION

PATENT NO. : 4,297,266
DATED : October 27, 1981
INVENTOR(S) : Robert L. Ibsen and William R. Glace It is certified that error appears in the above-identified patent and that said Letters Patent are hereby corrected as shown below:

Column 4, line 55, "stores" should read --stored--.

Column 8, line 23, between the table and "silica 0.01-0.04 micron" insert as a separate line --the particle sizes being approximately:--.

Signed and Sealed this

Twenty-sixth Day of January 1982

[SEAL]

Attest:

Attesting Officer

GERALD J. MOSSINGHOFF

Commissioner of Patents and Trademarks